United States Patent [19]
Wong

[11] Patent Number: 5,640,978
[45] Date of Patent: Jun. 24, 1997

[54] METHOD FOR PAIN RELIEF USING LOW POWER LASER LIGHT

[75] Inventor: Edmund Wong, Honolulu, Hi.

[73] Assignee: DioLase Corporation, Berkeley, Calif.

[21] Appl. No.: 788,604

[22] Filed: Nov. 6, 1991

[51] Int. Cl.$^6$ ..................................................... A24B 3/12
[52] U.S. Cl. ........................................................ 128/898
[58] Field of Search ................... 128/395–398, 128/907, 665; 606/2, 3, 15, 16

[56] References Cited

U.S. PATENT DOCUMENTS

| | | | |
|---|---|---|---|
| 4,232,678 | 11/1980 | Skovajsa | 128/907 |
| 4,561,440 | 12/1985 | Kubo et al. | 128/395 |
| 4,836,203 | 6/1989 | Muller et al. | 128/665 |
| 5,029,581 | 7/1991 | Kaga et al. | 128/398 |

OTHER PUBLICATIONS

Title: Effects of Helium–Neon Laser Irridation on Skin Resistance and Pain in Patient with Trigger Points in the Neck or Back Author: Snyder–Mackler et al Journal. Physical Therapy vol: v69 Issue: n5 Publication Date May 1989.

*Primary Examiner*—Aaron J. Lewis
*Attorney, Agent, or Firm*—Howard Cohen

[57] ABSTRACT

The invention comprises a method for treatment of chronic and referred pain such as chronic headaches and migraine headaches, as well as pain of the upper back, neck and shoulders, and lower back pain using low power laser light. The source of such referred pain involves microscopic and macroscopic tears in the periosteal-osseous junctions of the upper vertebrae, the scapula, and the skull. These lesions stimulate the generation of histamines, kinins, bradykinins, prostaglandin, proteolytic enzymes, seratonin, and other substances which cause numerous localized autonomic reactions, such as muscle spasm, ischemia, local inflammation, edema, as well as generalized reactions such as increased blood pressure, photophobia, nausea, blurred vision, copious mucous flow of the nose and sinus, and the like. The muscle spasms are responsible for transmitting the pain sensation to other portions of the body, and the systemic reactions are often associated with migraine-type headaches. The sites of the periosteal-osseous lesions can be correlated directly with the distant locus of the referred pain sensation. The laser energy is directed to the sites of the lesions to cause an increase in lymphatic circulation at the site of the causative lesion in response to the laser energy. Laser energy delivered to the site results in increased blood circulation and cellular metabolism in the area, which promotes more rapid healing of the lesion.

4 Claims, 2 Drawing Sheets

METHOD FOR PAIN RELIEF USING LOW POWER LASER LIGHT

BACKGROUND OF THE INVENTION

Although it is often said that the common cold is the most prevalent disease among humankind, it is also true that chronic pain is an affliction that is almost as prevalent. Chronic headaches, muscle pain, joint pain, and the like are experienced by most individuals, and many persons have such chronic pain on a daily or weekly basis.

It is interesting to note that most forms of chronic pain often are not traceable to a specific causative factor. The term "referred pain" has been used to describe pain that is experienced at a locus removed from the cause or lacking an identified cause. From the perspective of a treating physician, this situation leads to skepticism concerning the patient's complaints, and a tendency to dismiss the complaints as psychosomatic, neurological, or imagined. From the perspective of the patient, there is real suffering experienced on a regular basis, and often there is no medical treatment to relieve the pain. Frequently, medical treatment consists of drugs such as analgesics or muscle relaxers. These substances are systemic, and can have adverse side effects such as kidney toxicity, liver inflammation, gastrointestinal symptoms, and the like. Alternative treatments consist of chiropractic manipulations, acupuncture, physical therapy, stress relief regimens, and the like. These approaches to treatment have had limited success for most chronic pain sufferers.

Research conducted 40 to 50 years ago indicated that referred pain could be emulated in test subjects by injecting hypertonic saline solution into the interspinous ligaments and causing temporary inflammations of the periosteum at the points where muscle tissue extends from the upper spinal vertebrae to the skull and the scapula. Referred pain was produced at various sites remote from the injection points, and was virtually indistinguishable from the sensations described by chronic pain sufferers. Moreover, it was clear that induced inflammation of specific sites along the spinous processes resulted in pain sensation at corresponding specific sites throughout the body far removed from the cause, and that the pain sensation could also be induced in the form of headaches similar to migraine headaches. This research also established that the pain referral mechanism did not involve mere neural transmission. However, this promising early work apparently was not followed, and did not result in effective treatment modalities.

In recent years low power lasers have been introduced for pain relief. Generally speaking, low power lasers have been used to treat "trigger points"; i.e., neural pathways that serve the area in which the pain is experienced; or to treat directly the muscle, joint, or area in which the pain is experienced. Low power lasers have also been used to treat the traditional acupuncture points. These treatment approaches do not take into account the fact that referred pain is linked to a causative factor far removed from the site of the pain, and that the referred pain sensation is not transmitted by neural action. Low power lasers have enjoyed some success, but the potential for this treatment modality has not been realized due to a lack of consideration of the root cause of referred pain.

SUMMARY OF THE PRESENT INVENTION

The present invention generally comprises a method for treatment of chronic and referred pain using low power laser light. The method is particularly useful in treating chronic headaches and migraine headaches, as well as pain of the upper back, neck and shoulders, and lower back pain. A significant aspect of the invention is that the method treats the causative factor of the chronic or referred pain, so that the method achieves pain reduction or relief as well as reduction or removal of the causative factor of the pain.

It has been found that the source of referred pain such as headaches, backaches (upper and lower back), neck pain, and shoulder pain involves microscopic and macroscopic tears in the periosteal-osseous junctions of the upper vertebrae, the scapula, and the skull. These lesions stimulate the generation of histamines, kinins, bradykinins, prostaglandin, proteolytic enzymes, seratonin, and other substances. These substances cause numerous localized autonomic reactions, such as muscle spasm, ischemia, local inflammation, edema, as well as generalized reactions such as increased blood pressure, photophobia, nausea, blurred vision, copious mucous flow of the nose and sinus, and the like. The muscle spasms are responsible for transmitting the pain sensation to other portions of the body, and the systemic reactions are often associated with migraine-type headaches.

The site of the periosteal-osseous lesion usually can be correlated directly with the distant locus of the referred pain sensation. The present inventor has previously treated such lesions with injections of a combination of a local anesthetic, an anti-inflammatory steroid, and a muscle relaxant, and has obtained excellent results in relief and cure of chronic and referred pains. However, applying injections to all of the lesion sites is a tedious and time-consuming process, and some patients balk at injections. The present invention overcomes these drawbacks by introducing a treatment method in which a low power laser is used to project a laser beam through the skin and overlying tissue to the site(s) of the periosteal-osseous lesion(s). In contrast to prior art techniques of other practitioners, the treatment sites are neither "trigger points" (neural pathways), nor the site of the symptomatic pain, nor acupunture points. The laser beam is preferably in the near- to mid-infrared range, so that the beam penetrates the overlying tissue and reaches the lesion. The power levels used range from 30–150 milliwatts, with an upper limit of 500 milliwatts, and the treatment time ranges from a few seconds to an upper limit of 3–5 minutes. Treatment time, power level, and reiteration is correlated with the extent of the soft tissue lesions and the depth of the overlying muscle and tissue. Treatment may be terminated based on a timed dose of laser energy; however, the patient often spontaneously notices pain remission or relief, and treatment may be stopped at that time.

It is believed that the primary physiological mechanism that is responsible for the pain cessation is an increase in lymphatic circulation at the site of the causative lesion in response to the laser energy. Moreover, laser energy delivered to the site results in increased blood circulation and cellular metabolism in the area, which promotes more rapid healing of the lesion.

A notable advantage of the method of the present invention is that the laser treatment is sufficiently low in power that there is no possibility of tissue damage or other injury to the patient.

3

Figures 3, 4:
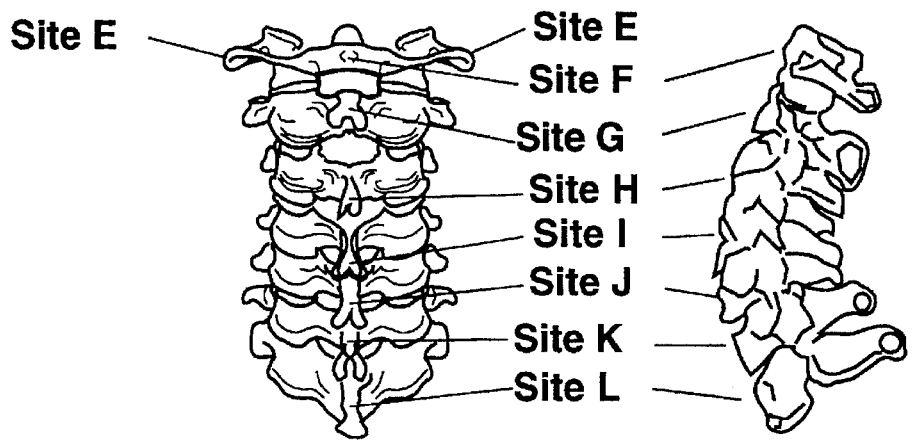

FIG. 3 is a posterior view of the cervical human vertebrae, showing low power laser treatment points in accordance with the method of the present invention.

FIG. 4 is a side elevation of the cervical human vertebrae, showing low power laser treatment points in accordance with the method of the present invention.

Figure 5:
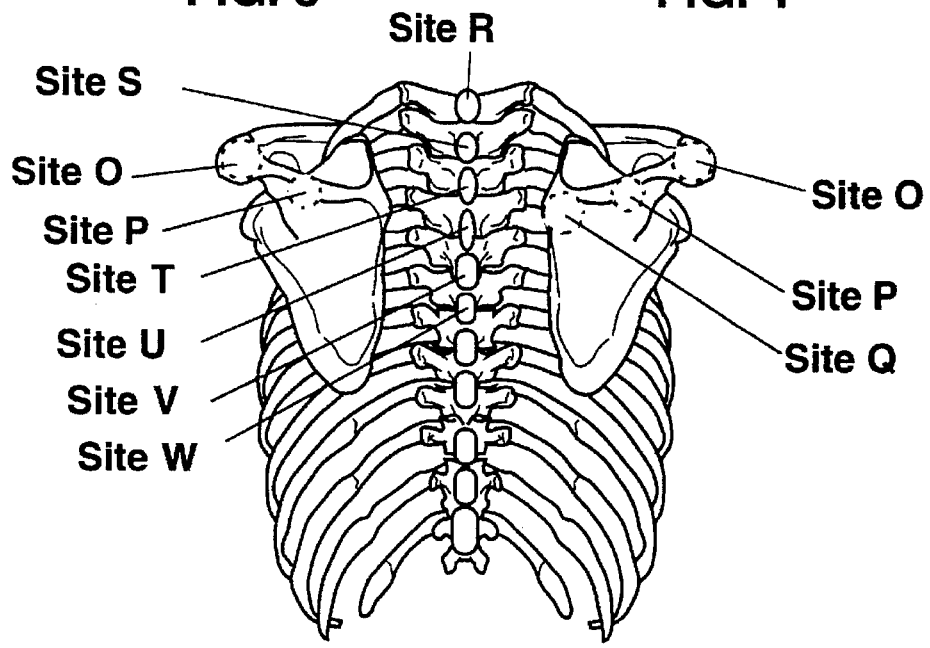

FIG. 5 is a posterior view of the upper human skeleton, showing low power laser treatment points in accordance with the method of the present invention.

Figure 6:
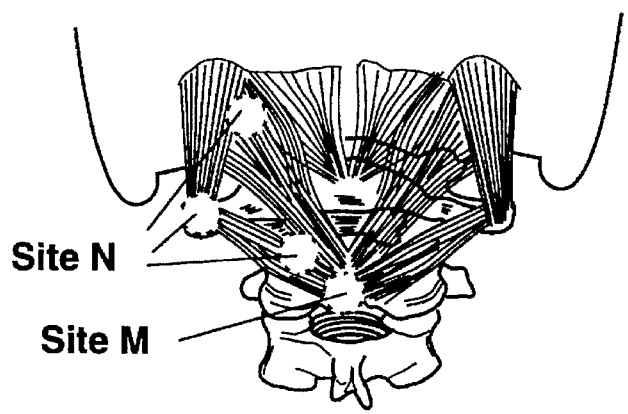

FIG. 6 is a posterior elevation of the sub-occipital triangle attachment of muscles, showing low power laser treatment points in accordance with the method of the present invention.

DESCRIPTION OF THE PREFERRED EMBODIMENT

The present invention generally comprises a method for treatment of chronic and referred pain using low power laser light. The method is particularly useful is treating chronic headaches and migraine headaches, as well as pain of the upper back, neck and shoulders, and lower back pain.

The method of the invention is based on the principle that the source of referred pain such as headaches, backaches (upper and lower back), neck pain, and shoulder pain involves microscopic and macroscopic tears in the periosteal-osseous junctions of the upper vertebrae, the scapula, and the skull. The injured tissues liberate histamines, kinins, bradykinins, prostaglandin, proteolytic enzymes, seratonin, and other substances. The resulting muscle spasms caused by these substances create pain sensations at locations which may be far removed from the insulting injury. Moreover, the site(s) of the periosteal-osseous lesion usually can be correlated directly with the locus of the pain sensation(s).

For example, the withdrawal reflex is the basis of neuro-muscular dysfunction causing chronic headaches, migraine headaches, and the like. Noxious chemical stimuli from soft tissue injuries at the nuchal line of the skull (FIG. 1) causes the occipitalis muscles to spasm and withdraw, activating the golgi end organs and muscle spindles of the occipitalis, and the anterior, posterior, and superior auricularis muscles. Tension placed on the aponeurosis of the scalp is extended to the frontalis and obicularis oculi muscles. The involvement of the auricularis muscles accounts for headache pain sensation at the sides of the head, and the involvement of the obicularis oculi muscles is the cause of pain sensations about the eyes. However, these pain sensations are due to soft tissue injuries along the nuchal line adjacent to the occipital protuberance.

Figure 2:
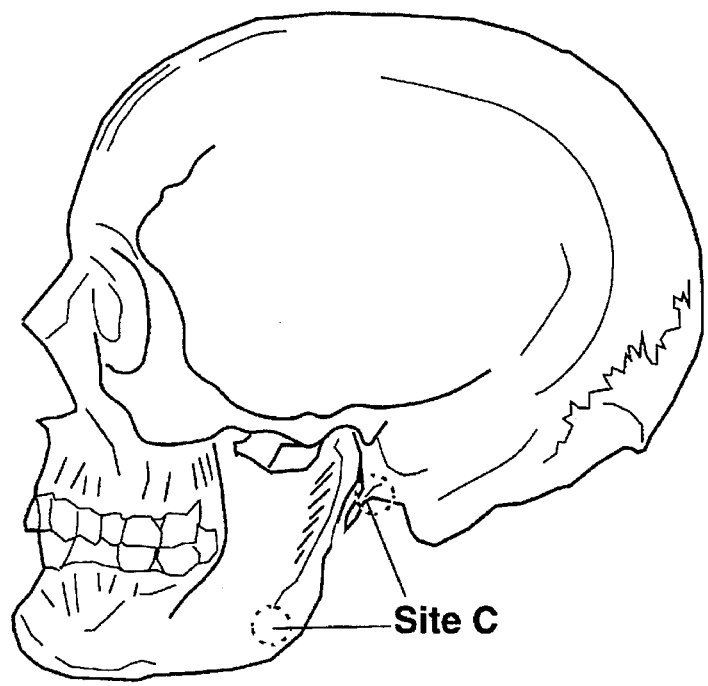
FIG. 2 is a side view of the human skull, showing low power laser treatment points in accordance with the method of the present invention.
Figure 1:
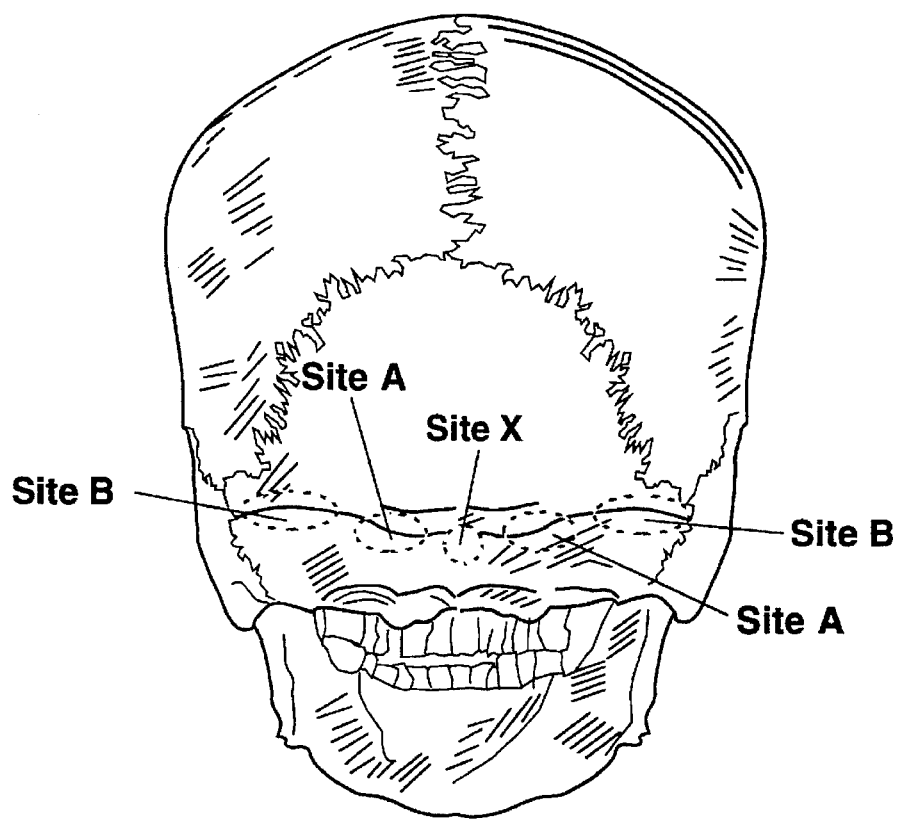
FIG. 1 is a rear view of the human skull, showing low power laser treatment points in accordance with the method of the present invention.

To treat the cause of headaches, low power laser energy is applied to sites indicated in the following Headache Treatment Chart and shown in FIGS. 1 and 2. The laser beam is preferably in the near- to mid-infrared range, so that it penetrates several millimeters in tissue and reaches the soft tissue injuries. The power levels used range from 30–150 milliwatts, with an upper limit of 500 milliwatts, and the treatment time ranges from a few seconds to an upper limit of 3–5 minutes. Treatment time, power level, and reiteration is correlated with the extent of the soft tissue lesions and the depth of the overlying muscle and tissue. Treatment may be terminated based on a timed dose of laser energy; however, the patient often spontaneously notices pain remission or relief, and treatment may be stopped at that time.

| HEADACHES | |
|---|---|
| Pain Location | Treatment Site |
| Occipital | Superior nuchal line of occipital bone and occipital protuberance - Sites A, X, B |
| Frontal headache, intra-ocular pains-lateral aspect of nasal bone | Nuchal line from occipital protuberance to medial ⅓ of superior nuchal line - Sites A, X |
| Temporal, Parietal and intra-ocular Pain | Lateral ⅓ of superior nuchal line, especially above mastoid process - Site B |
| Mastication Pain | Tip of the transverse process of C1; tips of styloid process and angle of the mandible (SMD) over TMJ - Site C |

The laser light acts to increase lymphatic circulation at the site of the soft tissue lesions, removing the noxious substances that cause the muscle spasms and withdrawal that are the root cause of the headache pain. The laser light also increases blood circulation and cellular metabolism to promote the healing of the lesions. If the lesions are allowed to heal, and are not re-injured, the causative factor will be removed and the headache symptoms will not recur.

Likewise, pains in the neck can be treated using low power laser energy to stimulate healing of the soft tissue injuries that are responsible for the pain sensations. The sites for treatment are indicated on the following chart and in FIGS. 1–4.

| Pain Location | Treatment Site |
|---|---|
| NECK PAIN | |
| Anterior Cervical | Styloid process and angle of mandible (SMD) Site C |
| Lateral Cervical | Lateral and inferior surface of mastoid process; tip of transverse process of C1; attachment of trapezius at nuchal line; tip of spinous process of C2 Sites D, E, F, G, and M |
| POSTERIOR CERVICAL PAIN | |
| Upper cervical-superficial pain | Medial ⅓ of nuchal line and occipital protuberance - Site A |
| Upper cervical-deep pain | Inferior surface of nuchal line from ligamentum nuchae to mastoid process - Site N |
| Lower cervical | Tips of spinous processes of C2 and C4–C7, medial and superior angle of scapula and spine and acromion process - Sites G, I, J, K, L, O, P, Q |

Many forms of lower back pain are also treatable in accordance with the method of the present invention. The most common sites for soft tissue injuries is at the inferior and superior surfaces of the spinous processes in acceleration and deceleration injuries. With these tears in the periosteum, hemorrhage can be expected, accompanied by release of histamines, bradykinins, serotonin, potassium ions, prostaglandins and the like. These substances become the noxious stimuli that cause the superficial and deeper paravertebral muscles to contract. The sustained contractions result in spasms that compress the vertebral disks. In the presence of subclinical herniated or protruding disks, muscle spasms cause the disk to protrude posteriorly, resulting in lower back or leg pain. If the disk protrudes laterally, the patient may complain of chest pain brought about by contraction and spasm of the intercostal muscles that extend anteriorly. This same mechanism is responsible for some parasthetic weakness of the arms, hands, and fingers.

In the case of lower back pain and parasthetic weakness, low level laser energy is applied to the site of the soft tissue injury(ies) to promote healing and removal of the causative factor. The treatment parameters are as described previously. Once treatment is completed, an external supportive device may be used to relieve stress in the area of the soft tissue injury undergoing healing, so that a cure is effected. The following chart indicates the appropriate treatment points as indicated in FIGS. 4–8.

| PARASTHETIC WEAKNESS PAINS OF EXTREMITIES | |
| --- | --- |
| Pain Location | Treatment Site |
| Upper arm and forearm | Tips of spinous process of C4 and C5 Sites C, I, and J |
| Hands and fingers | Tips of spinous process of C5, C6, C7 and T1 - Sites C, J, K, L, and R |
| Lower back, legs, and feet | Tips of spinous process of C6, C7 and T1 and/or T2, T3, T4, T5, and T6 Sites C, K, L, R, S, T, U, V, W |

For all of the treatment sites noted above for headache, neck, and extremities treatment, it may be helpful, but not necessary, to palpate the recommended treatment sites to detect any inflammation at the sites. Often the patient will notice tenderness, pain, or sensitivity upon touch or pressure applied to the treatment sites, although these sensations were not the presenting symptoms. Such a reaction is a good indication that these treatment sites are indeed loci of soft tissue injuries, and should be treated with low power laser light.

It should be noted that the method of the present invention is directed toward treating the causative factors for the pains described above, and is capable of effecting not only pain relief, but a cure for many chronic pain patients. No drugs, either local or systemic, are required, so that adverse drug reactions are eliminated as a risk of treatment. Furthermore, the low power laser energy is not capable of causing tissue damage or any other injury to the patient, and is thus an ideal treatment modality.

I claim:

1. A method for relief of pain caused by periosteal-osseous injuries that liberate inflammatory substances at the injury sites and cause muscle spasms and withdrawal that create pain at sites distant from said injury sites, comprising the steps of identifying said sites of periosteal-osseous injuries by palpation to distinguish said sites by localized tenderness, and irradiating the periosteal-osseous injury sites with low power laser energy to open lymphatic channels and remove the inflammatory substances so that the muscle spasm and withdrawal are alleviated and the referred pain is reduced.

2. The method for relief of pain of claim 1, wherein said low power laser energy is in the near-infrared to mid-infrared range.

3. The method for relief of pain of claim 1, wherein said low power laser energy is in the power range of 30 mW–150 mW.

4. The method for relief of pain of claim 1, wherein said low power laser energy has a minimum power of 30 mW and a maximum power of 500 mW.

* * * * *